(12) United States Patent
Rueckmann

(10) Patent No.: US 11,399,740 B2
(45) Date of Patent: Aug. 2, 2022

(54) TRAINING AND REHABILITATION INVOLVING PHYSICAL ACTIVITY AND COGNITIVE EXERCISES

(71) Applicant: Action Faction, Ltd., Dubai (AE)

(72) Inventor: Bogdan Von Rueckmann, Kuesnacht (CH)

(73) Assignee: Action Faction, Ltd., Dubai (AE)

( * ) Notice: Subject to any disclaimer, the term of this patent is extended or adjusted under 35 U.S.C. 154(b) by 0 days.

(21) Appl. No.: 16/937,842

(22) Filed: Jul. 24, 2020

(65) Prior Publication Data

US 2021/0177308 A1    Jun. 17, 2021

Related U.S. Application Data

(63) Continuation of application No. 15/619,613, filed on Jun. 12, 2017, now abandoned.

(Continued)

(51) Int. Cl.
*G09B 19/00* (2006.01)
*G09B 5/00* (2006.01)
(Continued)

(52) U.S. Cl.
CPC .......... *A61B 5/1118* (2013.01); *A61B 5/4088* (2013.01); *G09B 5/00* (2013.01); *G09B 19/0038* (2013.01); *G16H 20/30* (2018.01); *G16H 50/30* (2018.01); *G16H 50/50* (2018.01); *A61B 5/1038* (2013.01); *A61B 5/112* (2013.01); *A61B 5/1112* (2013.01); *A61B 5/486* (2013.01); *A61B 5/6898* (2013.01); *G09B 19/003* (2013.01)

(58) Field of Classification Search
None
See application file for complete search history.

(56) References Cited

U.S. PATENT DOCUMENTS 8,332,544 B1    12/2012  Ralls et al.
8,747,199 B1     6/2014  Palmisano et al.
(Continued)

OTHER PUBLICATIONS

"The Walk—Fitness Tracker and Game" by Six to Start; Accessed Sep. 6, 2017; https://itunes.apple.com/us/app/the-walk-fitness-tracker-and-game/id678971662?mt=8.

(Continued)

*Primary Examiner* — Robert J Utama
(74) *Attorney, Agent, or Firm* — Banner & Witcoff, Ltd.

(57) ABSTRACT

System, methods and electronic devices aimed at motivating users to perform physical activity are disclosed herein. A user may be presented with a series of physical and cognitive exercises. For example, an exercise may be locked until completion of an unlocked exercise. Performance in each exercise may be tracked to display feedback to a user and track the user's improvement over time. Physical exercises may comprise challenges to move a particular distance or take a particular number of steps. Cognitive exercises comprise techniques test or train the cognitive abilities of the user in: attention, memory, processing speed, logical reasoning, numerical reasoning, spatial reasoning, verbal reasoning, language, and cognitive executive functions. Performance in one exercise may modify the difficulty or parameters of a subsequent exercise. The tracking of user improvement may comprise a progress or reward system such as the increasing of a user's "level" or awarding of "badges."

27 Claims, 8 Drawing Sheets

Related U.S. Application Data

(60) Provisional application No. 62/349,311, filed on Jun. 13, 2016.

(51) Int. Cl.
*A61B 5/11* (2006.01)
*A61B 5/00* (2006.01)
*G16H 50/50* (2018.01)
*G16H 50/30* (2018.01)
*G16H 20/30* (2018.01)
*A61B 5/103* (2006.01)

(56) References Cited

U.S. PATENT DOCUMENTS

| | | | |
|---|---|---|---|
| 8,758,019 B2 | 6/2014 | Suzansky | |
| 8,764,532 B1 | 7/2014 | Berme | |
| 9,092,123 B1 | 7/2015 | Kahn et al. | |
| 9,474,970 B2 | 10/2016 | Kil et al. | |
| 2003/0144047 A1 | 7/2003 | Sprogis | |
| 2004/0180708 A1 | 9/2004 | Southard et al. | |
| 2005/0181340 A1 | 8/2005 | Haluck | |
| 2005/0181347 A1 | 8/2005 | Barnes et al. | |
| 2006/0025282 A1 | 2/2006 | Redmann | |
| 2007/0239479 A1 | 10/2007 | Arrasvuori et al. | |
| 2007/0254270 A1 | 11/2007 | Hersh | |
| 2008/0009349 A1 | 1/2008 | Wolfe | |
| 2009/0221928 A1 | 9/2009 | Einav et al. | |
| 2010/0035726 A1 | 2/2010 | Fisher et al. | |
| 2010/0216530 A1 | 8/2010 | Chudley et al. | |
| 2012/0046569 A1 | 2/2012 | Johnstone et al. | |
| 2012/0088216 A1 | 4/2012 | Wexler | |
| 2012/0238831 A1 | 9/2012 | Benford | |
| 2012/0253489 A1 | 10/2012 | Dugan | |
| 2012/0315987 A1 | 12/2012 | Walling | |
| 2013/0035613 A1 | 2/2013 | Curtiss | |
| 2013/0040714 A1 | 2/2013 | Rosing | |
| 2013/0216988 A1 | 8/2013 | You et al. | |
| 2013/0288223 A1 | 10/2013 | Watterson et al. | |
| 2014/0074454 A1 | 3/2014 | Brown et al. | |
| 2014/0199670 A1 | 7/2014 | Stack | |
| 2014/0276130 A1 | 9/2014 | Mirelman et al. | |
| 2014/0370479 A1 | 12/2014 | Gazzaley | |
| 2015/0037771 A1 | 2/2015 | Kaleal, III et al. | |
| 2015/0050626 A1 | 2/2015 | Tully | |
| 2015/0080131 A1 | 3/2015 | Bacon et al. | |
| 2015/0086953 A1 | 3/2015 | Johansson | |
| 2015/0148113 A1 | 5/2015 | Klein et al. | |
| 2015/0161511 A1 | 6/2015 | Ghassemzadeh et al. | |
| 2015/0208975 A1 | 7/2015 | Ghajar | |
| 2015/0251098 A1 | 9/2015 | Schwartz | |
| 2016/0005320 A1 | 1/2016 | deCharms et al. | |
| 2016/0078780 A1 | 3/2016 | Alexander et al. | |
| 2016/0256771 A1 | 9/2016 | Ekbia et al. | |
| 2016/0262680 A1 | 9/2016 | Martucci et al. | |
| 2016/0263439 A1 | 9/2016 | Ackland | |
| 2016/0267804 A1 | 9/2016 | Pemba et al. | |
| 2016/0283847 A1 | 9/2016 | Keohane et al. | |
| 2016/0293033 A1 | 10/2016 | Anderson-Hanley | |
| 2016/0302710 A1 | 10/2016 | Alberts et al. | |
| 2016/0321939 A1 | 11/2016 | Anantha et al. | |
| 2016/0321945 A1 | 11/2016 | DenBoer et al. | |
| 2016/0354683 A1 | 12/2016 | Palmisano et al. | |
| 2017/0103666 A1 | 4/2017 | Reichow et al. | |
| 2017/0124901 A1 | 5/2017 | Sasidhar et al. | |
| 2017/0124910 A1 | 5/2017 | Sasidhar et al. | |
| 2017/0229037 A1 | 8/2017 | Gazzaley | |
| 2017/0266502 A1 | 9/2017 | Aragones et al. | |
| 2017/0300663 A1 | 10/2017 | Paparella et al. | |
| 2017/0323523 A1 | 11/2017 | Hilbert et al. | |
| 2018/0028920 A1 | 2/2018 | Judkins et al. | |
| 2018/0070823 A1 | 3/2018 | Blackwell et al. | |

OTHER PUBLICATIONS

Feb. 15, 2018—U.S. Non-final Office Action—U.S. Appl. No. 15/696,906.

Ballesteros, 2017, "Effects of Video Game Training on Measures of Selective Attention and Working Memory in Older Adults: Results from a Randomized Controlled Trial"; https://www.ncbi.nlm.nih.gov/pmc/articles/PMC5671951/(Year: 2017).

Chang, "The Effects of Acute Exercise on Cognitive Performance: a meta analysis," (2012); <https://ac.els-cdn.com/S0006899312004003/1-s2.0-S0006899312004003-main.odf?_tid=f369f5da-e404-11e7-9f8f-00000aab0f26&acdnat=1513609737_7cce7342415e5b5c75a74b93e17ec2do.

Carlier, "Cognitive Benefits of Physical Activity Increased when producing rhythmic actions," 2014, <https://ac.els-cdn.com/S1877042814019399/1-s2.0-S1877042814019399-main.odf?+tid=ea577a66-e405-11e7-aff8-00000ab0f27&acdnat=1513610151_89f7b8bb7fbe4b353615252a571f7fab.

Lee, "Evolving methods to combine cognitive and physical training for individuals with mild cognitive impairment: study protocol for a randomized controlled study," 2016, <https://www.ncbi.nlm.nih.gov/pmc/articles/PMC5084379/.

Tait, "Influence of Sequential vs. Simultaneous Dual-Task Exercise Training on Cognitive Function in Older Adults," 2017, <https://www.ncbi.nlm.nih.gov/pmc/articles/PMC5681915/.

Nov. 23, 2018—U.S. Final Office Action—U.S. Appl. No. 15/619,613.

Feb. 15, 2018—U.S. Non-Final Office Action—U.S. Appl. No. 15/619,613.

Jun. 24, 2019—U.S. Non-Final Office Action—U.S. Appl. No. 15/619,613.

Jan. 24, 2020—U.S. Final Office Action—U.S. Appl. No. 15/619,613.

Nov. 23, 2018—U.S. Final Office Action—U.S. Appl. No. 15/696,906.

TRAINING AND REHABILITATION INVOLVING PHYSICAL ACTIVITY AND COGNITIVE EXERCISES

CROSS-REFERENCE TO RELATED APPLICATION

This application claims priority to U.S. Non-Provisional Patent Application Ser. No. 15/619,613, filed Jun. 12, 2017, which is a continuation of U.S. Provisional Patent Application Ser. No. 62/349,311, filed Jun. 13, 2016, and entitled "TRAINING AND REHABILITATION INVOLVING PHYSICAL ACTIVITY AND COGNITIVE EXERCISES," the disclosure of which is incorporated by reference herein in its entirety and made part hereof.

FIELD

Aspects of the invention relate to computerized training, rehabilitation programs, and more specifically, to mobile device applications aimed to increase the fitness level and/or cognitive abilities of participants.

BACKGROUND

It is well-known that many people in the Western world do not perform sufficient physical activity during their daily work or leisure time, and that this leads to a multitude of chronic health conditions like diabetes, obesity and cardiovascular diseases. Despite this knowledge, it is notoriously difficult for individuals to change their lifestyle and avoid the negative long-term consequences to their health.

Several factors are believed to be responsible for this difficulty in changing from a sedentary lifestyle to a more active one, which are mostly psychological in nature. Psychologists have been dealing with the prevention and treatment of disorders caused by physical inactivity by enrolling patients in behavioral lifestyle interventions, which provide counselling and guidance to individuals seeking to lead a healthier and more active life. Although effective for the individuals who actively participate in them, behavioral lifestyle interventions are plagued by the inconvenience of visiting the psychologist on a regular basis, by the lack of adherence to the protocol that participants need to follow between visits, and ultimately by high dropout rates.

Since the advent of smartphones, a number of activity tracking applications (apps) and associated wearables have been developed that aim to increase the awareness of individuals of their physical activity levels during the day and to point out deficiencies in the number of steps taken (as determined by pedometers) or in the number of calories burned (as determined by accelerometer-based physical activity monitors). Several data visualization tools have been developed that display individual physical activity levels across time, or compare them to specific benchmarks.

In order to make the user experience more enjoyable, in recent years, activity tracking apps started to incorporate social and gamification features. Initially employed as self-monitoring tools, the individual users of these activity tracking apps may now also communicate with each other in virtual communities, exchange their fitness results and offer support and encouragement to each other.

Further, in an effort aiming at increasing the engagement with activity tracking applications, several industry players started to implement gamification elements, and a few even developed fitness-related apps that look more like games. However, the game elements added to the fitness part of the programs so far belong to two categories: rewards (e.g. points, levels, badges) and social competition/cooperation (e.g. leaderboards).

Despite the wide adoption of activity tracking apps and wearables in the last years, there are still serious limitations regarding their efficacy to induce sustained lifestyle changes, with the majority of users showing suboptimal results or abandoning the usage after a few months. Although commercially successful, current mobile fitness apps and games are not addressing adequately the psychological factors involved in the behavioral change process of sedentary people. Therefore, there is still a significant unmet need in making these technologies more effective in their ability to motivate people to increase their physical activity. The system and methods described herein greatly reduce or eliminate the shortcomings described above.

BRIEF SUMMARY

Systems, methods, and electronic devices aimed at motivating users to perform physical activity are disclosed herein. These entail combining physical activity with cognitive exercises in specific ways, which may lead to increased user self-efficacy and intrinsic motivation, and therefore, may ultimately lead to increased levels of physical activity.

The approach disclosed herein involves compounding the challenge of performing physical activity by adding cognitive exercises in addition to a physical activity in a specific manner. In the context of physical activity, the performance increase of a sedentary user that is starting a physical activity program may be quite slow, and the relative comparison to the average physical activity levels of others might not be favorable at the beginning. Thus, lack of "immediate gratification" in perceiving progress, or even discouragement in the face of slow progress and poor comparative performance, may be major hurdles in improving self-efficacy. Due to the lack of self-efficacy, users may be less motivated to improve their fitness with current physical activity programs, apps and associated wearables.

Aspects of the present invention address the shortcomings typically encountered with fitness programs, apps, and associated wearables by incorporating cognitive exercises in the training program in such a way that participants may improve their self-efficacy along with other psychological factors, their motivation to participate in these computerized programs, and ultimately their level of physical activity. Aspects of the present invention may involve the integration of physical activity with cognitive exercises in such a manner that, although performed in an alternating way and over a period of time, the exercises may be perceived as a unitary behavior.

Initially, compounding physical activity with cognitive exercises may appear motivationally detrimental, as it may be increasing the difficulty of the tasks for the user rather than providing encouragement and rewarding the user for performing physical activity. However, the combined physical activity/cognitive exercise may actually be linked to psychological benefits that greatly outweigh the disadvantage of the increased effort required from users. In a comparative field test evaluating a conventional implementation of a program that rewarded users for performing physical activity exercises versus an essentially identical program that incorporated cognitive exercises on top of physical activity exercises, the group that performed additional cognitive exercises displayed far fewer dropout rates, and much higher increases in physical activity (e.g., measured in daily number of steps).

These effects may be attributed to increases in self-efficacy of the users faced with both physical activity and cognitive exercises. Self-efficacy stands out as a key construct in the psychology of physical activity. It may be defined as people's beliefs about their capabilities to complete tasks and reach goals (Bandura A. Self-efficacy: Toward a Unifying Theory of Behavioral Change. Psychol Rev 1977; 84: 191-215.). Self-efficacy may be central to several theories applied in behavioral lifestyle research, e.g. Social Cognitive Theory, Protection Motivation Theory, Theory of Planned Behavior and Health Action Process Approach. One recent review of these psychological theories may be found in "Psychology of Physical Activity: Determinants, Well-Being and Interventions" by Stuart J. H. Biddle, Nanette Mutrie and Trish Gorely (third edition 2015 by Routledge).

In numerous studies, self-efficacy may be shown as a good predictor of the adoption and maintenance of physical activity behavior in healthy adults. Therefore, self-efficacy may be used in order to increase a specific behavior. Self-efficacy techniques may include providing feedback on past performance or providing feedback in comparison to others' performance, as long as one's performance is perceptibly increasing in time and comparing favorably to the performance of others.

The integration of physical and cognitive exercises may be crucial for the purpose of transferring psychologically motivating factors from one component of the integrated behavior to another. Specifically, the two components of the behavior, namely physical activity and cognitive exercises, may be associated with different feedback cycles: physical activity may include long feedback loops of weeks, or even months, before a progress becomes visible and the benefits associated with increased levels of physical fitness are perceived. In contrast, improvements in cognitive exercises may be much faster, such that improvements in performing cognitive tasks may be evident within days, or even hours. The short feedback loops of cognitive exercises may be linked with faster feelings of achievement, a boost in confidence, and an increase in self-efficacy. In order for this increase in self-efficacy to extend to the physical activity component of the behavior as well, the two component behaviors may need to be closely entangled in the training program.

Aspects of the current invention provide several methods for integrating physical exercises and cognitive exercises within a training and rehabilitation system and apparatus with the purpose of creating synergistic benefits between the two components. These methods may involve one or more of the following:

1. Including user tasks that comprise both physical activity and cognitive exercises,
2. Unlockable cognitive exercises that may be contingent upon the prior completion of a physical exercise,
3. Unlockable physical exercises that may be contingent upon the prior completion of a cognitive exercise,
4. Variable cognitive exercise features/parameters that may be dependent upon the prior completion of a physical exercise or upon the performance attained in a prior physical exercise,
5. Variable physical exercise features/parameters that may be dependent upon the prior completion of a cognitive exercise or upon the performance attained in a prior cognitive exercise,
6. Generation of a combined score comprising a physical exercise sub-score and/or a cognitive exercise sub-score, and
7. Generation of a combined progress parameter or indicator (e.g. degree of program completion, level, rank) that may depend both on the performance attained in physical exercises and on the performance attained in cognitive exercises.

In addition to the motivating effects on physical activity, aspects of the present invention may also increase the efficacy of cognitive exercises, as increased levels of physical activity may improve people's brain plasticity, and therefore, cognitive performance. Physical activity may lower dementia risk, cause the release of brain-derived neurotrophic factor (BDNF), which may stimulate the growth of new neurons, and may cause the release of irisin, a hormone linked to improved cognitive function.

Aspects of the present invention may describe a program that combines physical activity with cognitive exercises in a synergistic manner, such that users may be motivated to engage more often and for longer periods of time in physical exercises, thereby increasing their fitness levels. Conversely, the synergistic effects of increased physical activity may benefit the cognitive function and augment the efficacy of the performed cognitive exercises. For example, the same dose of cognitive exercises, linked with the physical activity component, may cause a greater beneficial effect on cognition compared to a situation when the cognitive exercises had been performed in an isolated manner, without the linked physical activity component.

Aspects of the current invention may also be used in cases of rehabilitation that may require physical and/or mental recuperation. Several cardiovascular disorders, brain injuries, or ailments of the locomotor system may benefit from the techniques, methods and systems described herein.

Aspects of the invention describe a program that integrates physical activity and cognitive exercises in a way that benefits both the physical activity performance and the cognitive training performance, much more than if physical activity and cognitive exercises had been performed in isolation from each other.

BRIEF DESCRIPTION OF THE DRAWINGS

A more complete understanding of aspects described herein and the advantages thereof may be acquired by referring to the following description in consideration of the accompanying drawings, in which like reference numbers indicate like features, and wherein.

DETAILED DESCRIPTION

In the following description of the various embodiments, reference is made to the accompanying drawings, which form a part hereof, and in which is shown by way of illustration various embodiments in which aspects described herein may be practiced. It is to be understood that other embodiments may be utilized and structural and functional modifications may be made without departing from the scope of the described aspects and embodiments. Aspects described herein are capable of other embodiments and of being practiced or being carried out in various ways. Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof. The use of the terms "mounted," "connected," "coupled," "positioned," "engaged" and similar terms, is meant to include both direct and indirect mounting, connecting, coupling, positioning and engaging.

Figure 1:
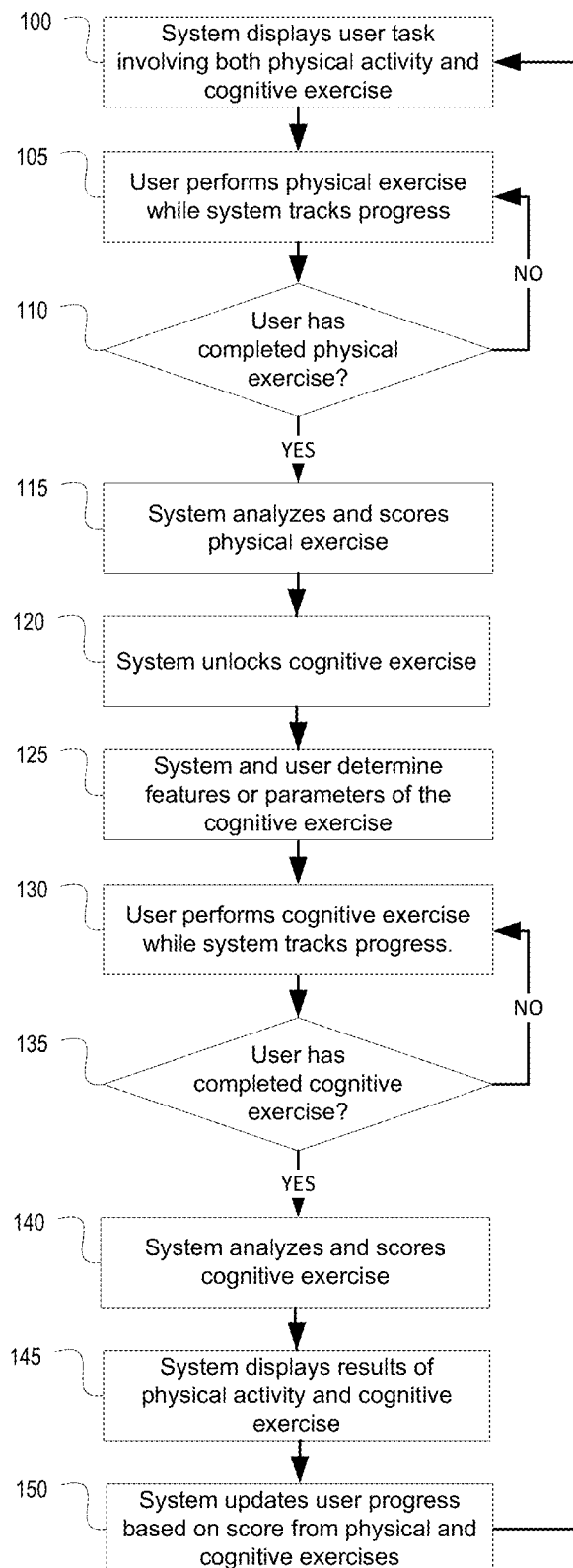
FIG. 1 illustrates a method, according to one embodiment, of combining a series of physical and cognitive exercises provided to a user, tracking the user's performance on those exercises, and displaying results of those exercises to the user.

FIG. 1 illustrates a method, according to one embodiment, of combining a series of physical and cognitive exercises provided to a user, tracking the user's performance on those exercises, and displaying results of those exercises to the user.

In step 100, the system may use a user interface screen to display a task involving a physical exercise and/or a cognitive exercise. The system may receive physical exercises and/or cognitive exercises from a server. After receiving the physical exercises and/or cognitive exercises, a task may be displayed to the user. The task may include a physical exercise and/or a cognitive exercise. For example, the displayed task on the user device may be: "Walk briskly for 30 minutes and then exercise your memory for 5 minutes." Additionally, and/or alternatively, the displayed task on the user device may be more generic, and hint towards the underlying physical activity and/or cognitive exercise rather than displaying the explicit parameters. For example, the task may be: "Walk to the next waypoint and get the secret password." In this case, "walk to the next waypoint" may imply 30 minutes of walking. Further, "get the password" may imply a 5 minute memory exercise that may be revealed at a later stage, such as after completing the 30 minutes of walking. In some examples, the physical exercise and/or cognitive exercise may automatically commence without user input. In some embodiments, the physical exercise and/or cognitive exercise may be designed to begin upon receiving a user input indicating assent to the physical exercise and/or cognitive exercise (e.g., by selecting a generated user interface element indicating the exercise, clicking or tapping an actual button or button of a generated user interface, pressing a hotkey corresponding to the exercise, or issuing a verbal command that may be detected by a microphone and interpreted by the system).

In some instances, the system may be designed to alternate between physical exercises and cognitive exercises. For example, an "unlocked" and a "locked" exercise may be displayed on the user device. The "unlocked" and "locked" exercises may be a multitude of different physical exercises and/or cognitive exercises. For example, a physical exercise or a cognitive exercise may be "locked" until the "unlocked" exercise (e.g., another physical exercise or cognitive exercise) has been completed, at which point the "locked" physical exercise or the cognitive exercise may be "unlocked." The locked status may be indicated, on the user device, by a generated user interface that allows the user to see the existence or details of the locked exercise, but marks the exercise with an icon (e.g., a visual representation of a closed padlock or a key), color (e.g., "graying out" the exercise), text, and/or other visual effects. The system may also display future or subsequent physical exercises and/or cognitive exercises, which may remain locked until the current physical exercise and/or cognitive exercise is completed.

The physical exercise may comprise the user taking a certain number of steps (e.g., 1,000, 5,000, 6,000, or 10,000 steps), travelling a predetermined distance (e.g., 1 mile, 2 miles, 5 kilometers, 5 miles, or a half-marathon [13.1 miles]), traversing a certain number of vertical steps (e.g., 50, 100, or 200 steps of a staircase), and/or burning an estimated number of calories through physical activity (e.g., 100 calories, 200 calories, or 300 calories). The physical exercise may be performed by walking, jogging, running, or other locomotion such as using a bicycle, roller skates/blades, or skateboard. The user may have a time period to perform the physical exercise. For example, the physical exercise may be performed over a definite time period such as an hour, a day, a two-day period, or a week. In some instances, the user may have unlimited time to perform the physical exercise.

The cognitive exercise may comprise techniques used to test and/or train the cognitive abilities of the user in one or more of the following domains: attention, memory, processing speed, logical reasoning, numerical reasoning, spatial reasoning, verbal reasoning, language and cognitive executive functions. The psychological techniques that are effective in testing and/or training cognitive abilities have been investigated extensively in clinical studies and described in the psychological literature. In some examples, cognitive exercises may include: for attention "Multiple Object Tracking" and "Useful Field of View"; for memory "Complex Span" and "Dual N-Back"; and so forth. In some instances, cognitive exercises may include a series of arithmetic problems, extrapolating or interpolating patterns to identify missing elements, matching exercises of examining a multitude of elements and identifying common features, memorizing a series of numbers or other elements, logic puzzles, and/or identifying synonyms, antonyms, or translations of words.

In some embodiments, cognitive exercises may be untimed (e.g., with a user goal of accurately answering as many questions as possible), timed, but with a hard time limit (e.g., with a user goal of answering as many correct answers as possible within a time limit), or timed, but with no time limit (e.g., with a goal of minimizing the time to answer exercises while maximizing accuracy).

In some examples, the difficulty level of the physical exercise and/or the cognitive exercise may be adjusted based on the user. For example, the difficultly level may be based on the user's previous accuracy and speed, such that a training effect occurs, and the user improves and remains engaged with the exercises. In some instances, the difficulty level of the physical exercise and/or the cognitive exercise may be adjusted based on the attributes for the user. For example, a user may input user attributes, such as height, weight, and/or age. The system may store the user attributes and change the difficulty level based on the stored user attributes. In some embodiments, the difficulty level of the physical exercise and/or the cognitive exercise may be adjusted based on user input. For example, a user may input a difficulty level (e.g., easy, medium, hard, extra hard) for the physical exercise and/or the cognitive exercise. The system may adjust the difficulty level based on the user input.

In step 105, the user may begin performing the unlocked exercise. For example, the unlocked exercise may be the physical exercise. The system may receive an indication to begin the physical exercise. After receiving the indication, the system, using one or more sensors of a user device and/or one or more sensors connected to the user device, may detect and/or record the user's physical activity. For example, a multiple-axis accelerometer may be used as a pedometer to determine the number of steps taken by the user since the physical exercise commenced. In some examples, a global positioning system (GPS) receiver of the device may track user's location over time to determine a total distance traveled by the user since the physical exercise commenced. The system may display determined statistics via a generated user interface, such as a total number of steps taken since the exercise commenced, a total number of steps taken by the user in all exercises, a total distance traveled by the user since the physical exercise commenced, a total distance traveled by the user in all exercise, a total number of calories burned in the current exercise, a current location of the user, and/or a percentage or fraction of the current physical exercise that has been completed.

In some examples, the unlocked exercise may be the cognitive exercise. As explained in further detail below, the system may detect and/or record the cognitive exercise performed by the user. After the user completes the cognitive exercise, and the system scores the cognitive exercise, the system may unlock the locked physical exercise.

In step 110, the system may determine, periodically, whether the unlocked exercise (e.g., the physical exercise) has been completed. For example, the system may check multiple times per second, once per second, multiple times per minute, once a minute, or more rarely or frequently. The system may track the user's progress and update any user interfaces displaying information to the user until the requirements for the physical exercise is met.

Once the system determines the user has completed the unlocked exercise (e.g., the physical exercise), in step 115, the system may analyze the recorded performance of the user and determine a numerical and/or qualitative sub-score for the unlocked exercise (e.g., the physical exercise). The sub-score may be based on the amount of time taken to complete the exercise as compared to a goal time, the amount and/or the intensity of the physical exercise (e.g., taking 5,000 running steps), and/or the distribution of the physical activity over time (e.g., whether the user was active during many hours or only during a short period of time). The sub-score may be a percentage (e.g., a percentage of the total exercise completed within a goal time or a percentile ranking of the user compared to other users), an integer (e.g., a certain number of points per step or a certain number of points per minute taken less than a goal time), a value indicating a ranking (e.g., "A", "B", or "C", or gold, silver, or bronze), and/or another numerical representation.

The system, after determining the physical exercise sub-score, may display the sub-score and/or other statistics related to the performance of the physical exercise (e.g., time taken, steps taken, distance traveled, calories burned, or a map showing the user's path) on the user device. The system may additionally display, on the user device, that the physical exercise has been completed (e.g., displaying a message or animation, causing a tactile vibration, and/or playing an audio cue).

In some instances, the system may generate a reward for the user. For example, the system, based on the sub-score for the physical exercise, may generate a reward for the user. The reward may assist the user in completing a later exercise, such as a subsequent physical and/or cognitive exercise. For example, the reward may allow a user more time to complete the exercise, allow a user another attempt to complete the exercise, and/or allow a user to skip or defer the exercise. In some instances, the reward may be given to another player. For example, and explained in further detail below, the system may include a multiplayer feature. The multiplayer feature may include multiple players performing the physical and/or cognitive exercises. Rewards from one player may be transferred to another player to assist the other player in performing the physical and/or cognitive exercises.

In step 120, after completing the unlocked exercise, the system may notify the user that the locked exercise has been unlocked. For example, after completing the physical exercise, the system may indicate that the previously locked exercise (e.g., the cognitive exercise) may be unlocked and ready to be performed. The system may display a message or animation, play an audio cue, cause a tactile vibration, change the color or text of the cognitive exercise in the user interface, or remove a "locked" indicator icon on the cognitive exercise in the user interface to indicate that the user may begin. In some instances, the cognitive exercise may be the unlocked exercise and the physical exercise may be the locked exercise. After completing the cognitive exercise, the system may unlock and/or display the "locked" physical exercise.

In step 125, after "unlocking" the previously "locked" exercise, the system and/or the user may determine whether to proceed with default parameters for the previously locked exercise. In some embodiments, the system may modify the default parameters of the previously "locked" exercise. For example, the physical exercise may be the unlocked exercise. After the user completes the physical exercise, the cognitive exercise (e.g., the previously locked exercise) may be unlocked. Certain characteristics of the physical exercise may influence parameters of the subsequent cognitive exercise. For instance, the physical exercise may be completed within a predetermined time limit, and the system may reward the user with an allocation of extra time in the subsequent cognitive exercise. In some examples, the system may reward the user based on the performance of the physical exercise with hints to one or more subsequent exercises, fewer challenges to perform in the given time, extending the choice of cognitive exercises to be performed, giving the user greater flexibility in performing the exercise, and/or other changes designed to make the cognitive exercise more rewarding. Additionally, and/or alternatively, the user may select parameters to make the exercise more challenging, such as increasing the number or difficulty of the challenges to perform, decreasing a time limit, or imposing other restrictions. The rewards or options generated by the system in response to the performance of the physical exercise may incentivize better physical exercise performances in the future, and may also increase the integration between the two exercise components of a training program.

In some examples, the cognitive exercise may be the unlocked exercise. After the user completes the cognitive exercise, the physical exercise (e.g., the previously locked exercise) may be unlocked. Certain characteristics of the cognitive exercise may influence parameters of the subsequent physical exercise. For instance, the cognitive exercise may be completed within a predetermined time limit, and the system may reward the user with an allocation of extra time in the subsequent physical exercise. In some examples, the system may reward the user for a good cognitive exercise performance with hints to one or more subsequent exercises, fewer challenges to perform in the given time, extending the choice of physical exercises to be performed, and/or other changes designed to make the physical exercise more rewarding or giving the user greater flexibility in performing the exercise. Additionally, and/or alternatively, the user may select parameters to make the exercise more challenging, such as increasing the number or difficulty of the challenges to perform, decreasing a time limit, or imposing other restrictions. The rewards or options generated by the system in response to a good cognitive exercise performance may incentivize better cognitive exercise performances in the future and also increase the integration between the two exercise components of a training program.

In step 130, after the parameters of the previously locked exercise are determined, the system may receive a user indication that the user may be ready to perform the previously locked exercise. For example, similar to commencing with the unlocked exercise, the system may receive user input indicating assent to begin the exercise (e.g., by clicking or tapping an actual button or button of a generated user interface, pressing a hotkey corresponding to the exercise, or issuing a verbal command that may be detected by a microphone and interpreted by the system). The system may begin providing challenges for the user to perform, according to the parameters determined in step 125. For example, the previously locked exercise may be the cognitive exercise. The system may record, using a timer, the challenge and/or for the set of challenges, and may determine whether an input answer to the cognitive exercise is correct. The system may display determined statistics via a generated user interface, such as a total number of correct answers, a total number of wrong answers, a percentage of correct answers, a percentage of all challenge answered so far, a time remaining or elapsed for the current challenge, or a total time remaining or elapsed for the entire cognitive exercise.

In step 135, the system may periodically determine whether the previously locked exercise (e.g., the cognitive exercise) has been completed. For example, the system may check after each cognitive challenge, of a set of challenges, if the cognitive exercise has been completed. Additionally, and/or alternatively, the cognitive exercise may include a time limit, and the system may check a timer multiple times per second, once per second, multiple times per minute, once a minute, or more rarely to determine whether the time limit has elapsed. The system may track the user's progress and update any user interfaces displaying information to the user until the user completes the cognitive exercise (e.g., completion of all challenges or the timer elapses).

In step 140, the system may analyze the recorded performance of the user and determine a numerical or qualitative sub-score for the previously locked exercise (e.g., the cognitive exercise). For example, the cognitive exercise sub-score may be based on the amount of time taken to complete the exercise as compared to a goal time, the average level of difficulty for all the challenges comprising the cognitive exercise, the number of cognitive challenges performed in the given time, or the number of errors committed while performing the cognitive exercise. The sub-score may be a percentage (such as a percentage of the total challenges completed within a goal time, or a percentile ranking of the user compared to other users), an integer (such as a certain number of points per correct answer or a certain number of points per minute taken less than a goal time), a value indicating a ranking (such as "A", "B", or "C", or gold, silver, or bronze), or another numerical representation.

In step 145, the physical exercise sub-score, as well as any recorded data regarding performance in the physical exercise, and the cognitive exercise sub-score, as well as any recorded data regarding performance in the cognitive exercise, may be evaluated by the system to determine an overall training score. The overall training score may be a mathematical combination of the two sub-scores (such as a sum or average of two numerical values), may be based on the greater or lesser of the two sub-scores (such as awarding a gold medal in the physical and a bronze medal in the cognitive exercise an overall training score of gold, or bronze, respectively), and/or may be converted from one type of sub-score to a different type of overall training score (such as awarding an overall training score of "A" if a user gets a physical sub-score of 91% and a cognitive sub-score of 95%). The overall training score may be purely a function of the two sub-scores, or may incorporate other inputs such as the user's previous performances, improvement of the user over time, or a scoring bonus earned from a previous performance in a physical or cognitive exercise. The overall training score may be displayed to the user, and may be accompanied by the sub-scores of the two exercises, or data or statistics regarding the performance in the two exercises. A graph, table, or other visual representation may be generated to portray the progress of the user in the training program over time.

In step 150, the system may also use the overall training score or any other measure based on the performance attained in the physical and cognitive exercises to calculate the progress of the user in the training program. The progress may be portrayed as a numerical parameter, such as the percentage completion of a part of the training program, as part of a "leveling" system or other reward system, whereby the program may provide rankings, badges, additional content or other rewards for the progress. The overall training score, or any other measure based on the performance attained in the physical and cognitive exercises of the user, may be also used as comparative measure with other users undergoing the training program. For instance, the overall training score may be used for ranking in a competition among several users or as basis for a leaderboard.

After the user has completed both the physical exercise and the cognitive exercise, the system may return to step 100, with a newly unlocked exercise (e.g., physical exercise or cognitive exercise) paired with a newly locked exercise (e.g., physical exercise or cognitive exercise).

In some examples, the system may include a story mode feature, such as displaying a mission on the user device. The mission may include multiple cognitive exercises and multiple physical exercises to be completed in succession, and the method, as described in FIG. 1, may be completed multiple times. For example, the story mode feature may include multiple unlocked and locked exercises for a user to complete. The parameters of the unlocked and locked exercises may be interdependent or related to each other. For example, based on past recorded data of a user performing physical and/or cognitive exercises, the system may modify the default parameters of new unlocked or locked exercises (e.g., the physical exercise and/or the cognitive exercise). The modified default parameters may be based on the sub-score of the cognitive exercise, the physical exercise, and/or the composite score of the cognitive exercise and physical exercise. In some instances, the system may modify the default parameters of the cognitive exercise and/or physical exercise if a previous iteration's physical exercise sub-score and/or cognitive exercise sub-score is above a certain pre-defined threshold. In some examples, the system may modify the default parameters of the cognitive exercise and/or physical exercise if a previous iteration's physical exercise sub-score and/or cognitive exercise sub-score is below a certain pre-defined threshold. By modifying the default parameters of the cognitive exercise and/or the physical exercise, the system may make the next iteration of the method described in FIG. 1 more or less challenging.

In some embodiments, the system may select new physical exercises and/or new cognitive exercises based on past recorded data (e.g., the sub-score of the cognitive exercise, the physical exercise, and/or the composite score of the cognitive exercise and physical exercise). For example, the system may select a more challenging exercise if the composite score of the physical exercise and the cognitive exercise, in the previous iteration, is above a certain pre-defined threshold. In some examples, the system may select a less challenging exercise if the composite score of the physical exercise and the cognitive exercise, in the previous iteration, is below a certain pre-defined threshold.

In some instances, the system may include a multiplayer feature. The multiplayer feature may allow multiple users, in various geographical areas, to perform the cognitive exercise and/or physical exercise. The system may allow the user to compete on cognitive and physical exercises with other users. For instance, prior to starting the cognitive exercises, physical exercises, and/or the story mode feature, the system may receive an indication that the user would like to join a group of users. The group of users may be friends of the user (e.g., social network application friends) or may be based on a geographic area (e.g., within a certain radius of the user device). After the user joins the group of users, the user may perform cognitive exercises and/or physical exercises. The exercises may be scored (e.g., sub-scores and/or composite scores of the physical exercise and cognitive exercise). These scores associated with the user may be compared with scores from the group of users. For example, the system may receive the scores, including the score associated with the user, from the group users. After receiving the scores, the system may rank the scores and display them in a leaderboard graphical interface. In some embodiments, the system may give rewards and/or other encouragement to entice the user to complete new cognitive exercises and/or physical exercises (e.g., by giving the user incentives).

Figure 2:
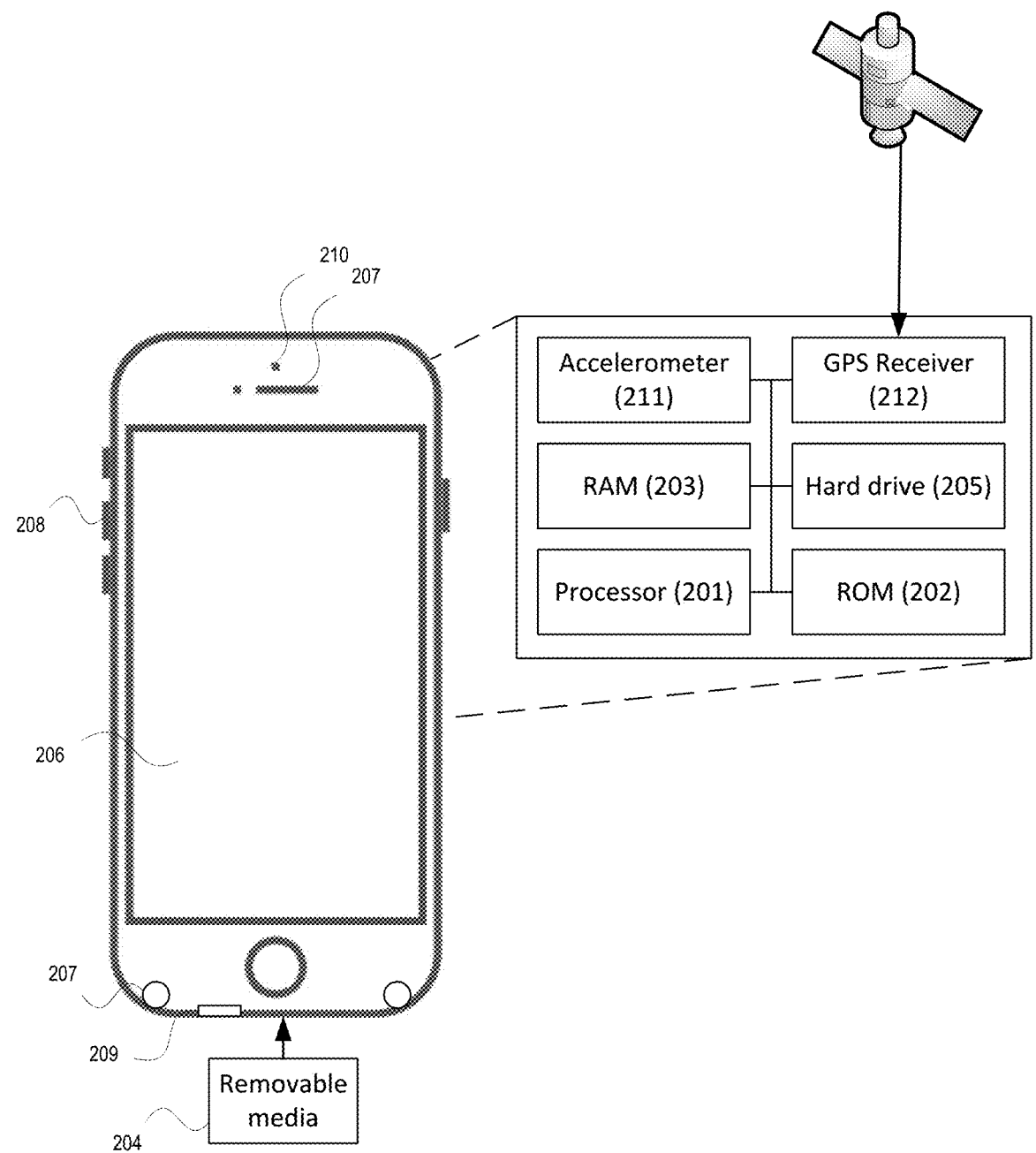
FIG. 2 illustrates general hardware elements that may be used to implement any of the various systems or computing devices discussed herein.

FIG. 2 illustrates general hardware elements that may be used to implement any of the various systems or computing devices discussed herein. A mobile computing device 200 may include one or more processors 201, which may execute instructions of a computer program to perform any of the features described herein. The instructions may be stored in any type of computer-readable medium or memory, to configure the operation of the processor 201. For example, instructions may be stored in a read-only memory (ROM) 202, random access memory (RAM) 203, removable media 204, such as a secure digital (SD) card or any other desired storage medium. Instructions may also be stored in an internal hard drive 205. The mobile computing device 200 may include one or more output devices, such as a display 206 or one or more speakers 207. There may also be one or more user input devices 208, such as a number of buttons, as well as a microphone 209, a touchscreen built into display 206, a camera input 210 for user gestures. The mobile computing device 200 may comprise sensors, including a multiple-axis accelerometer 211 or a global positioning system (GPS) receiver 212.

The FIG. 2 example is only one possible hardware configuration, and modifications may be made to add, remove, combine, divide, etc. components of mobile computing device 200 as desired. Multiple devices in communication with each other may be used, such as a mobile device in communication with a server or desktop computer over the Internet or another network, or a mobile device communicating with multiple sensors in other physical devices via Bluetooth, near field communications, or other wireless or wired communications protocols. Mobile computing device 200 may be a custom-built device comprising one or more of the features described above, or may be a wearable device, such as a smart watch or fitness tracking bracelet, with custom software installed, or may be a smartphone or other commercially available mobile device with a custom "app" or other software installed.

One or more aspects of the disclosure may be embodied in a computer-usable data and/or computer-executable instructions, such as in one or more program modules, executed by one or more computers or other devices. Generally, program modules include routines, programs, objects, components, data structures, etc. that perform particular tasks or implement particular abstract data types when executed by a processor in a computer or other data processing device. The computer executable instructions may be stored on one or more computer readable media such as a hard disk, optical disk, removable storage media, solid state memory, RAM, etc. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects of the disclosure, and such data structures are contemplated within the scope of computer executable instructions and computer-usable data described herein.

Figure 3A:
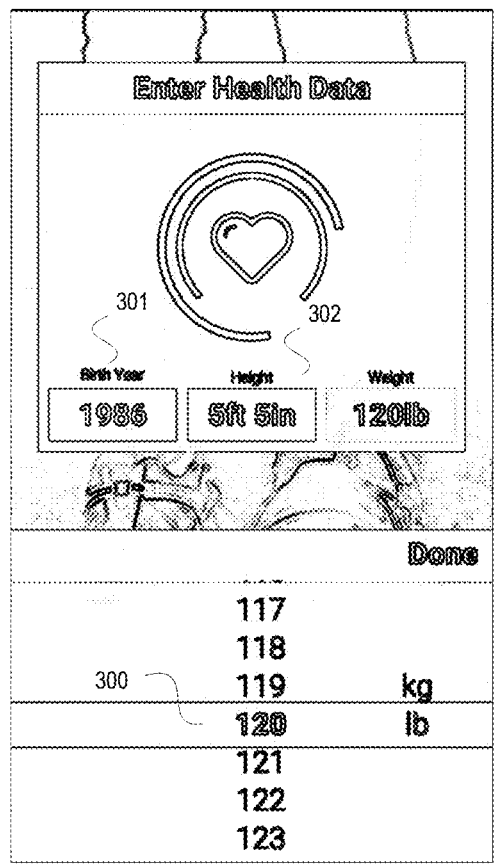
FIGS. 3A-B show illustrative output on a visual display during initialization of a device according to aspects described herein.
Figure 3B:
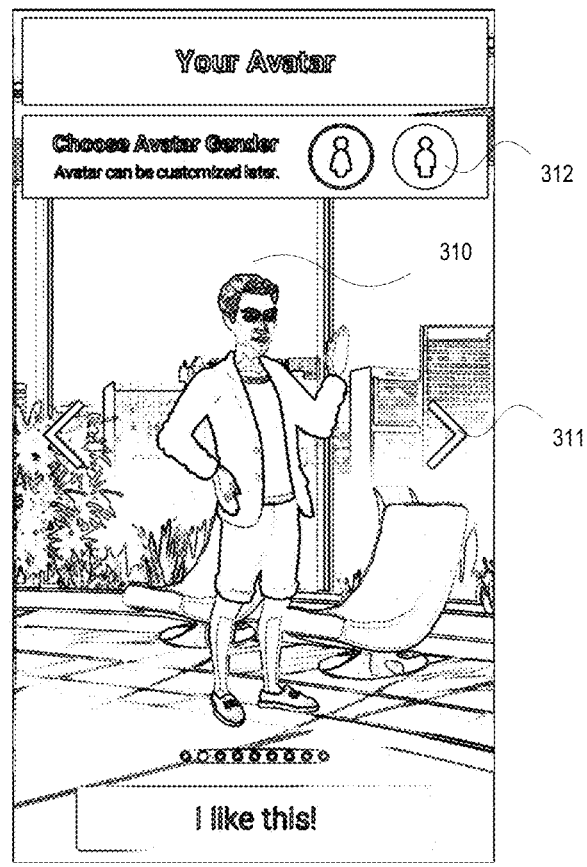

FIGS. 3A-B show illustrative output on a visual display during initialization of a device according to aspects described herein.

In FIG. 3A, a user may be prompted upon their first use of a device to select their weight/mass 300, their birth year 301, and their height 302, enabling estimations of calories burned, estimation of overall health status, and potentially allowing scoring a user in comparison to a cohort of other users with a similar body type or age.

In FIG. 3B, a user may be prompted to select an avatar 310 that represents them in the series of exercises. A number of possible avatars may be viewed using a slide show progression 311 controlled by the user, and the user may select a gender 312 for the avatar as well. User engagement with the device may be heightened if they feel a rapport with their avatar or feel more immersed in the displays of the device.

Figure 4A:
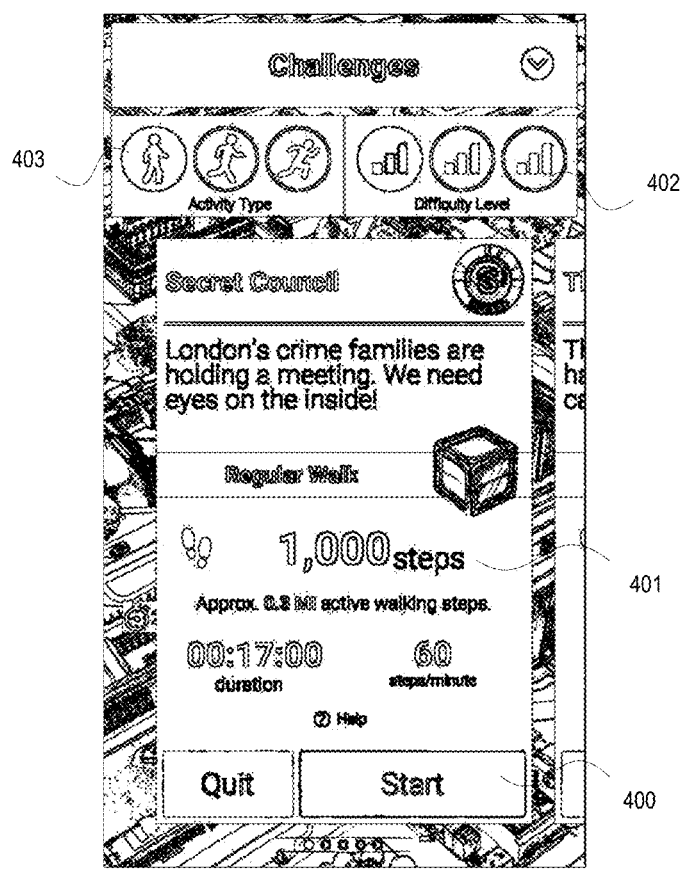
FIGS. 4A-B show illustrative output on a visual display during selection of and performance of a physical exercise.
Figure 4B:
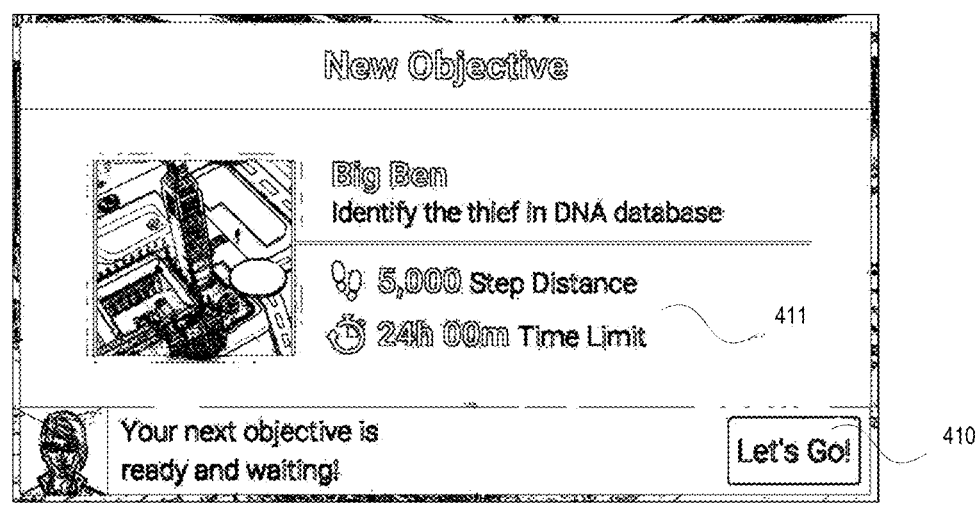

FIGS. 4A-B show illustrative output on a visual display during selection of and performance of a physical exercise.

In FIG. 4A, a user may be prompted to select a physical exercise to perform when a physical exercise is unlocked, and may be permitted to select a difficulty level 402 (which may influence the amount of time permitted to complete the exercise, an amount of physical activity/exertion required, or other aspects of the difficulty) and an activity type 403, which may be, for example, walking, jogging, or sprinting.

After viewing the summary of the exercise 401, which may include a total distance, total number of steps, and/or duration of the exercise, as well as derived statistics to help the user evaluate the exercise, such as the number of necessary steps per minute to achieve the exercise, the user may begin the exercise by selecting a start button 400.

In alternative embodiments, such as that illustrated by FIG. 4B, a user may immediately be presented with a new exercise after completing a previous exercise, without options to customize the exercise or its difficulty. The user may be presented simply with a summary of the exercise 411 and a button to begin the exercise 410.

Figure 5A:
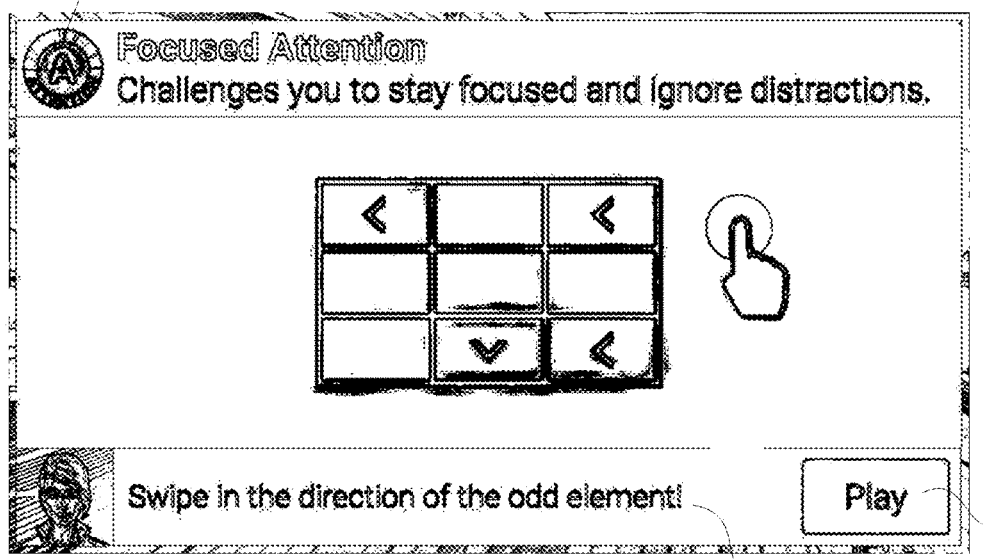
FIGS. 5A-B show illustrative output on a visual display during selection of and performance of a cognitive exercise.
Figure 5B:
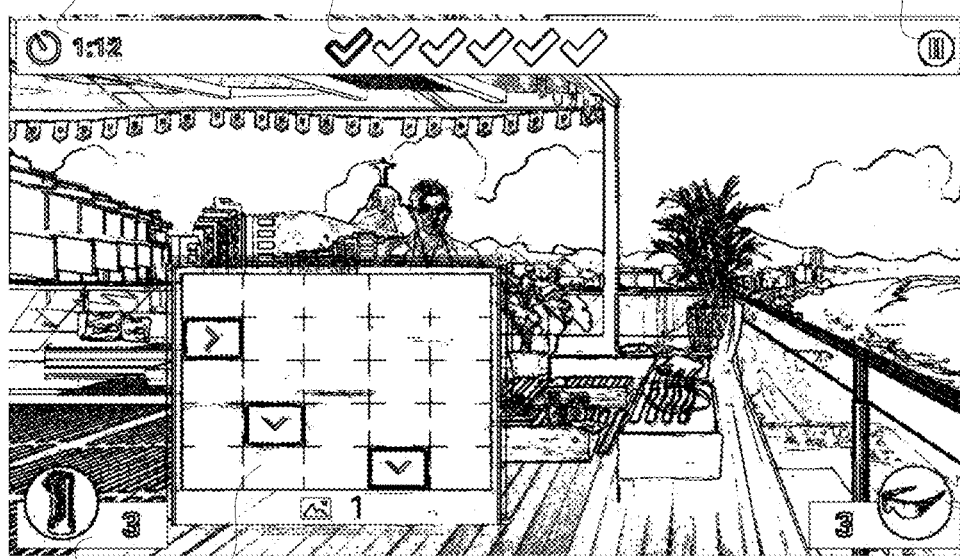

FIGS. 5A-B show illustrative output on a visual display during selection of and performance of a cognitive exercise.

FIG. 5A depicts a display describing a cognitive exercise that is about to begin. The display may comprise an icon 502 indicating the exercise type. For example, in some embodiments, the exercise's type may be "speed," "memory," "attention," "reasoning," or "talking." The icon may use a first letter of the exercise type to remind the user of what aspect of cognitive function will be tested/trained. The display may comprise instructions 501 to accompany an illustration of the exercise, and a button 500 to begin the exercise when the user is ready.

FIG. 5B depicts a cognitive exercise underway. A timer 510 may be used to indicate an amount of time remaining before failing the exercise, or an amount of time taken thus far. A progress bar 511 may use a series of checkmarks or other icons to indicate how many total subparts the exercise comprises, and how many have been completed or remain. The display may comprise a pause button 512 to allow the user to pause the timer mid-exercise; in some embodiments, a difficulty level may remove the pause button. Other user interface elements 513 and 514 may allow the user to affect the exercise, such as requesting a hint, skipping a current subpart of the exercise, or changing the exercise to increase or decrease its difficulty. The exercise itself may be performed by manipulating screen area 515 in accordance with the instructions 501.

Figure 6A:
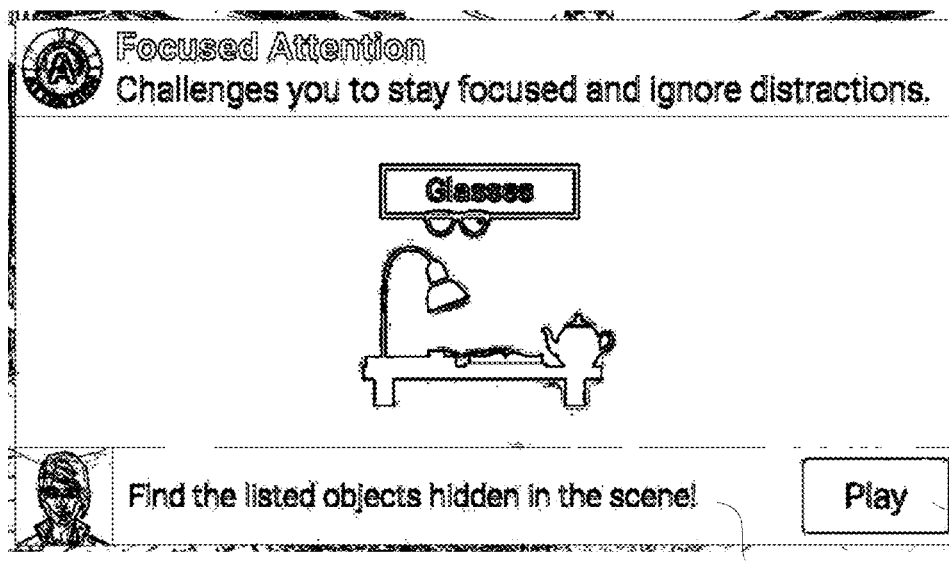
FIGS. 6A-B show illustrative output on a visual display during selection of and performance of another cognitive exercise.
Figure 6B:

FIGS. 6A-B show illustrative output on a visual display during selection of and performance of another cognitive exercise.

FIG. 6A depicts a display describing another cognitive exercise that is about to begin. The display may also comprise an icon indicating the exercise type. The display may comprise instructions 601 to accompany an illustration of the exercise, and a button 600 to begin the exercise when the user is ready.

FIG. 6B depicts the other cognitive exercise underway. The timer, progress bar, pause button, and other user interface elements may be present as in the first example of a cognitive exercise. The exercise itself may be performed by selecting hidden objects listed in goal display 610 from the display in accordance with the instructions 601 during a maximum allowable time.

Figure 7A:
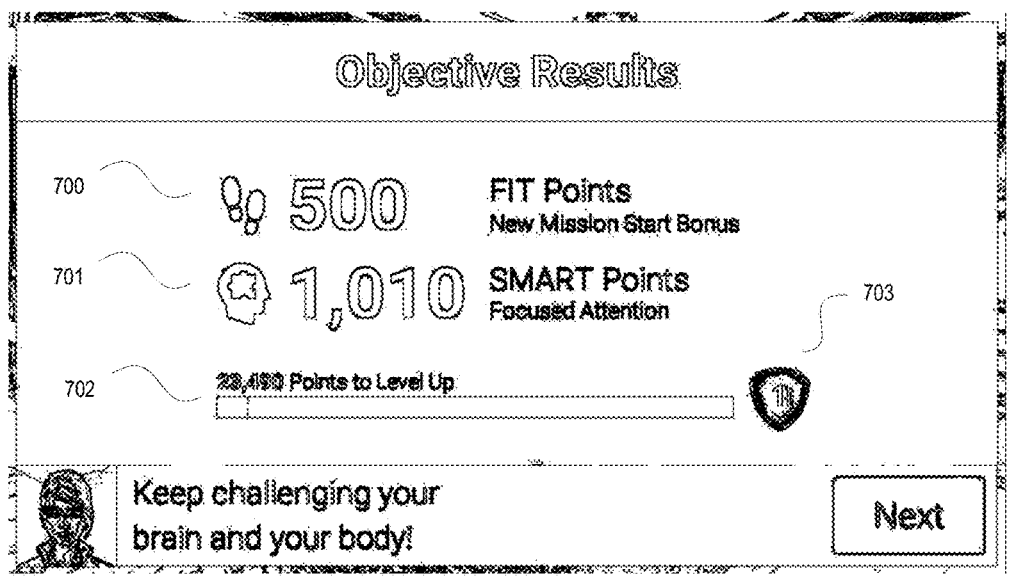
FIGS. 7A-C show illustrative output on a visual display recording or scoring a user's progress.
Figure 7B:
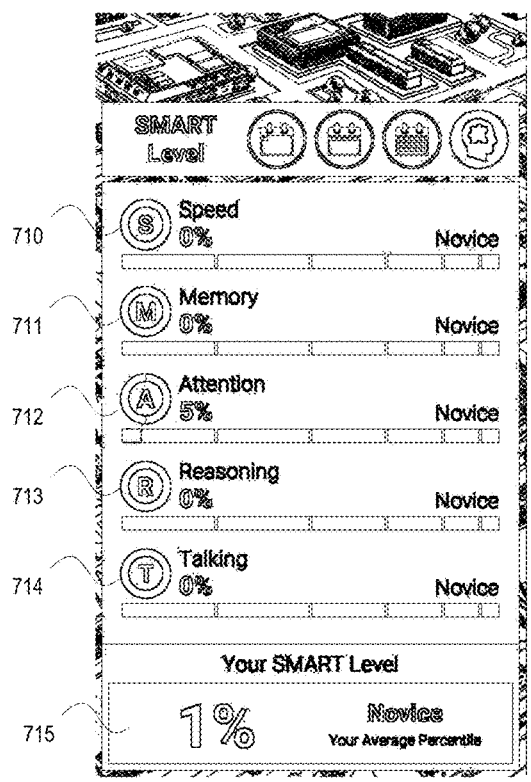
Figure 7C:
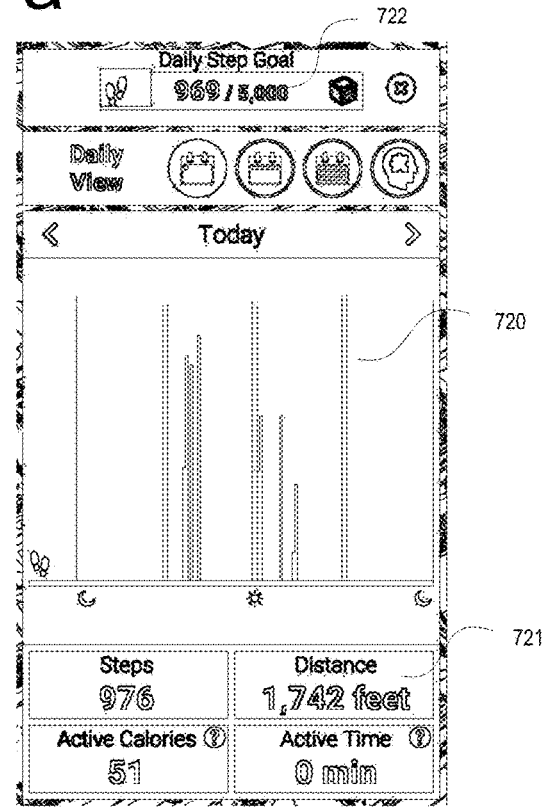

FIGS. 7A-C show illustrative output on a visual display recording or scoring a user's progress.

FIG. 7A depicts a scoring screen according to step 145, wherein a number of points 700 have been assigned for performance in the physical exercise, a number of points 701 have been assigned for performance in the cognitive exercise, and a total number of points have been credited to the user, as shown by progress bar 702, and level indicator 703. The progress bar may indicate a total number of points received, a total number of points remaining until the next level-up, or merely graphically display an increase in an implicit value that is not displayed. As a user's level increases, more options, difficulty levels, or exercise may be unlocked, and other customization such as changes to an avatar may be possible.

FIG. 7B depicts a progress screen for cognitive exercises. A user may be assigned a level and score in each cognitive exercise type, and a series of progress bars 710-714 may display those levels and scores in each type. An overall level and score 715 may be determined by averaging, adding, or otherwise incorporating the type scores to give an overall measure of cognitive performance.

FIG. 7C depicts a progress screen for physical progress. A graph 720 may show total physical activity plotted over time, for example, over the course of a day, week, month, or all time. Other data displays 721 may include a distance traveled, a number of steps taken, a total number of active minutes, or a number of active calories (such as additional calories over a basal metabolic rate) burned during the time period displayed. A daily step goal 722 may update in real time, showing progress towards completing a particular physical exercise which is underway, or a general progress even if no physical exercise is active.

Figure 8:
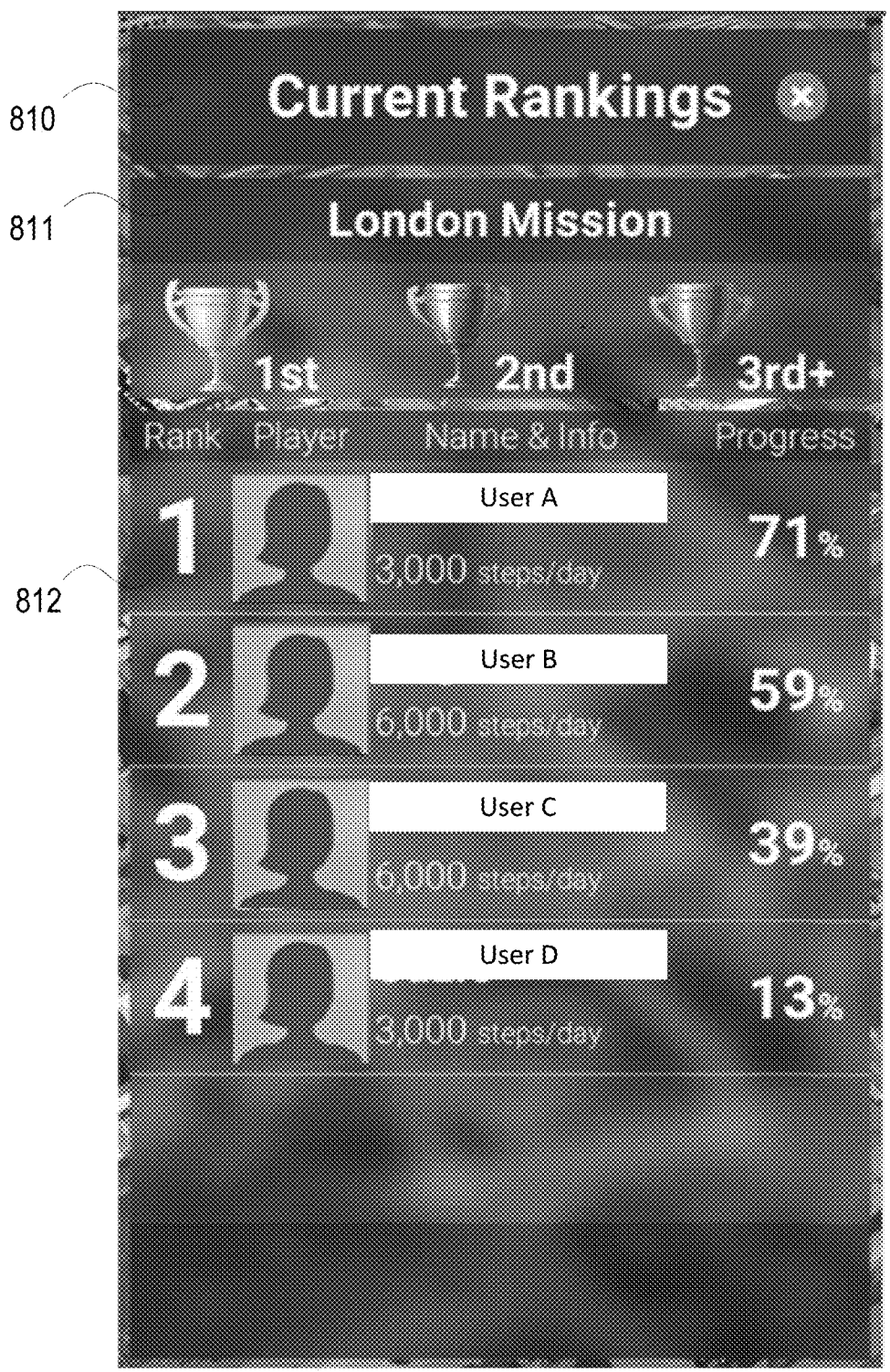
FIG. 8 shows illustrative output on a visual display for a multiplayer feature.

FIG. 8 shows illustrative output on a visual display for a multiplayer feature. For example, multiple users may be performing the same mission (e.g., same story mode feature). The graphical interface may display the current rankings 810 of multiple users. Additionally, the graphical interface may display the mission (e.g., London Mission) 811. The multiple users may be ranked 812 by the completion progress of the mission, which may represent a composite indicator for completing both physical exercises as well as cognitive exercises. Additionally, and/or alternatively, the rankings 812 may be based on the composite score of the cognitive exercise and physical exercise, the sub-score of the physical exercise, and/or the sub-score of the cognitive exercise. Further, the name of the user and the information (e.g., the number of steps per day for the user) may be displayed. The number of steps per day for the user may be based on the average number of steps the user takes in a given time period (e.g., the average number of steps per day for the user in the past two weeks).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method of fitness testing and training, comprising:
    recording, by a user device and using one or more sensors associated with the user device, first data corresponding to a user performing a physical exercise;
    preventing, in an interface associated with the user device, user access to a cognitive exercise task associated with training cognitive abilities of the user;
    determining, using the one or more sensors, that the physical exercise is complete;
    modifying, based on the first data, one or more parameters of the cognitive exercise task to provide more time to the user to complete the cognitive exercise task;
    enabling, in the interface and based on determining that the physical exercise is complete, the user access to the cognitive exercise task;
    recording, via the interface, second data corresponding to the user performing a cognitive exercise corresponding to the cognitive exercise task; and generating, based on the second data, feedback for display via the interface.

2. The method of claim 1, further comprising:
selecting the cognitive exercise from a plurality of cognitive exercises based on the first data.

3. The method of claim 1, wherein the physical exercise comprises walking a predetermined number of steps.

4. The method of claim 1, wherein the cognitive exercise comprises a test of at least one of: information processing speed, attention span, memory, problem solving, or language skills.

5. The method of claim 1, wherein the one or more sensors comprise a multiple-axis accelerometer.

6. A method of fitness testing and training, comprising:
recording, by a user device, first data corresponding to a user performing a cognitive exercise associated with training cognitive abilities of the user;
preventing, in an interface associated with the user device, user access to a physical exercise task;
determining, via the interface and based on the first data, that the cognitive exercise is complete;
modifying, based on the first data, one or more parameters of the physical exercise task to provide more time to the user to complete the physical exercise task;
enabling, in the interface and based on determining that the cognitive exercise is complete, the user access to the physical exercise task;
recording, using one or more sensors associated with the user device, second data corresponding to the user performing a physical exercise corresponding to the physical exercise task; and
generating, based on the second data, feedback for display via the interface.

7. The method of claim 6, further comprising:
selecting the physical exercise task from a plurality of physical exercise tasks based on the first data.

8. The method of claim 6, wherein the physical exercise task comprises walking a predetermined number of steps.

9. The method of claim 6, wherein the cognitive exercise comprises a test of at least one of: information processing speed, attention span, memory, problem solving, or language skills.

10. The method of claim 6, wherein the one or more sensors comprise a multiple-axis accelerometer.

11. A method of fitness testing and training, comprising:
preventing, in an interface associated with a user device, access to a one or more cognitive exercise tasks associated with training cognitive abilities of the user;
recording, by the user device and using one or more sensors associated with the user device, first data corresponding to a user performing one or more physical exercises;
modifying, based on the first data, one or more parameters of the one or more cognitive exercise tasks to provide more time to the user to complete the cognitive exercise task;
enabling, in the interface and based on determining that the one or more physical exercises are complete, the user access to the one or more cognitive exercise tasks;
recording, via the interface, second data corresponding to the user performing one or more cognitive exercises corresponding to the one or more cognitive exercise tasks;
determining, by the user device and based on the first data, a physical performance of the user performing the one or more physical exercises;
determining, by the user device and based on the second data, a cognitive performance of the user performing the one or more cognitive exercises;
calculating, based on the physical performance of the user and the cognitive performance of the user, a composite physical-cognitive score of the user performing the one or more physical exercises and the one or more cognitive exercises;
comparing the composite physical-cognitive score of the user with similarly determined overall scores of other users in at least one of: a ranking system, a competitive setting, or a leaderboard setting; and
providing, based on the comparing and via the interface, a number of rewards to the user.

12. The method of claim 11, further comprising:
transmitting, by the user device and to a server, the composite physical-cognitive score of the user.

13. The method of claim 11, wherein the physical exercise task comprises walking a predetermined number of steps.

14. The method of claim 11, wherein the cognitive exercise task comprises a test of at least one of: information processing speed, attention span, memory, problem solving, or language skills.

15. The method of claim 11, wherein the one or more sensors comprise a multiple-axis accelerometer.

16. A non-transitory computer readable medium comprising instructions that, when executed by one or more processors, cause a fitness testing and training device to:
prevent, via an interface associated with the fitness testing and training device, access to a cognitive exercise task associated with training cognitive abilities of a user;
record, using one or more sensors associated with the fitness testing and training device, first data corresponding to the user performing a physical exercise;
provide, based on the first data and via the interface, feedback on a first performance of the user performing the physical exercise;
modify, based on the first data, one or more parameters of the cognitive exercise task to provide more time to the user to complete the cognitive exercise task;
responsive to receiving an indication that the user completed the physical exercise, provide, via the interface and based on the first data, access to the cognitive exercise task;
record second data corresponding to the user performing a cognitive exercise corresponding to the cognitive exercise task; and
provide, via the interface and based on the second data, feedback on a second performance of the user performing the cognitive exercise.

17. The non-transitory computer readable medium of claim 16, further comprising:
selecting the cognitive exercise task from a plurality of cognitive exercise tasks based on the first data.

18. The non-transitory computer readable medium of claim 16, wherein the physical exercise comprises walking a predetermined number of steps.

19. The non-transitory computer readable medium of claim 16, wherein the cognitive exercise task comprises a test of at least one of: information processing speed, attention span, memory, problem solving, or language skills.

20. A non-transitory computer readable medium comprising instructions that, when executed by one or more processors, cause a fitness testing and training device to:
prevent, via an interface associated with the fitness testing and training device, access to a physical exercise task;

record first data corresponding to a user performing a cognitive exercise associated with training cognitive abilities of the user;

provide, based on the first data and via the interface, feedback on a first performance of the user performing the cognitive exercise;

modifying, based on the first data, one or more parameters of the physical exercise task to provide more time to the user to complete the physical exercise task;

responsive to receiving an indication that the user completed the cognitive exercise, provide, via the interface and based on the first data, the access to the physical exercise task;

display, via the interface, an indication of the physical exercise task;

record, using one or more sensors associated with the fitness testing and training device, second data corresponding to the user performing a physical exercise corresponding to the physical exercise task; and provide, via the interface and based on the second data, feedback on a second performance of the user performing the physical exercise.

21. The non-transitory computer readable medium of claim 20, further comprising:

selecting the physical exercise task from a plurality of physical exercise tasks based on the first data.

22. The non-transitory computer readable medium of claim 20, wherein the physical exercise task comprises walking a predetermined number of steps.

23. The non-transitory computer readable medium of claim 20, wherein the cognitive exercise comprises a test of at least one of: information processing speed, attention span, memory, problem solving, or language skills.

24. A non-transitory computer readable medium comprising instructions that, when executed by one or more processors, cause a fitness testing and training device to:

prevent, in an interface of the fitness testing and training device, access to a cognitive exercise task;

record, using one or more sensors associated with the fitness testing and training device, first data corresponding to a user performing one or more physical exercises corresponding to a physical exercise task;

modifying, based on the first data, one or more parameters of the cognitive exercise task to provide more time to the user to complete the cognitive exercise task;

enabling, in the interface and based on determining that the one or more physical exercises are complete, the user access to the cognitive exercise task;

recording, via the interface, second data corresponding to the user performing one or more cognitive exercises corresponding to the cognitive exercise task;

determine, based on the first data, a physical performance of the user performing the one or more physical exercises;

determine, based on the second data, a cognitive performance of the user performing the one or more cognitive exercises;

calculate, based on the physical performance of the user and the cognitive performance of the user, a composite physical-cognitive score of the user performing the one or more physical exercises and the one or more cognitive exercises; and provide, via the interface and based on the composite physical-cognitive score, a number of rewards to the user.

25. The non-transitory computer readable medium of claim 24, wherein the composite physical-cognitive score for the user is compared with a plurality of similar scores for a plurality of other users in at least one of: a ranking system, a competitive setting, or a leaderboard setting.

26. The non-transitory computer readable medium of claim 24, wherein the physical exercise task comprises walking a predetermined number of steps.

27. The non-transitory computer readable medium of claim 24, wherein the cognitive exercise task comprises a test of at least one of: information processing speed, attention span, memory, problem solving, or language skills.

* * * * *

UNITED STATES PATENT AND TRADEMARK OFFICE
CERTIFICATE OF CORRECTION

| | |
|---|---|
| PATENT NO. | : 11,399,740 B2 |
| APPLICATION NO. | : 16/937842 |
| DATED | : August 2, 2022 |
| INVENTOR(S) | : Rueckmann |

It is certified that error appears in the above-identified patent and that said Letters Patent is hereby corrected as shown below:

In the Claims

Column 15, Claim 6 Line 14:
After "comprising", insert --:--

Signed and Sealed this
Twenty-second Day of November, 2022

Katherine Kelly Vidal
*Director of the United States Patent and Trademark Office*